(12) United States Patent
Lappin et al.

(10) Patent No.: US 7,344,699 B2
(45) Date of Patent: Mar. 18, 2008

(54) DRUG CONJUGATE COMPRISING AN ERYTHROPOIETIN RECEPTOR LIGAND AND AN ANTICANCER AGENT

(75) Inventors: Terence Lappin, Hillsborough (GB); John Mann, Hollywood (GB); Michael McManus, Black Rock (AU); Perry Maxwell, Northern Ireland (GB)

(73) Assignee: The Queen's University of Belfast (GB)

( * ) Notice: Subject to any disclaimer, the term of this patent is extended or adjusted under 35 U.S.C. 154(b) by 0 days.

(21) Appl. No.: 10/515,248

(22) PCT Filed: May 21, 2003

(86) PCT No.: PCT/GB03/02194

§ 371 (c)(1),
(2), (4) Date: Sep. 26, 2005

(87) PCT Pub. No.: WO03/097106

PCT Pub. Date: Nov. 27, 2003

(65) Prior Publication Data

US 2006/0057063 A1    Mar. 16, 2006

(30) Foreign Application Priority Data

May 21, 2002  (GB) .................................. 0211578.0

(51) Int. Cl.
*A61K 38/18* (2006.01)
*A61K 49/14* (2006.01)
*A61K 51/04* (2006.01)
*C07K 14/505* (2006.01)

(52) U.S. Cl. ................. 424/1.41; 424/9.341; 424/85.1; 514/8; 514/21; 530/351

(58) Field of Classification Search ..................... None
See application file for complete search history.

(56) References Cited

U.S. PATENT DOCUMENTS 6,221,608 B1    4/2001  Johnson et al.

FOREIGN PATENT DOCUMENTS

| WO | WO 98/10650 | 3/1998 |
| WO | WO 00/61164 | 10/2000 |
| WO | WO 00/67769 | 11/2000 |

OTHER PUBLICATIONS

Haroon et al. Functional significance of erythropoietin receptor expression in breast cancer. Blood. Nov. 16, 2001, vol. 98 (11 Part 1), pp. 300a-301a.*
Kayser et al. Analysis of expression of erythropoietin-binding sites in human lung carcinoma by the biotinylated ligand. Zentralblatt fur Pathologie. Sep. 1992, vol. 138, No. 4, pp. 266-270.*
Wognum et al. Increased Erythropoietin-Receptor Expression . . . Blood. Feb. 1, 1992, vol. 79, No. 3, pp. 642-649.*
Kratz, et al.; "Synthesis of new maleimide derivatives of daunorubicin and biological activity of acid labile transferring conjugates"; Bioorganic & Medicinal Chemistry Letters, Oxford, GB; Mar. 4, 1997; vol. 7, No. 5, pp. 617-622.
Roodman, et al.; "DNA polymerase activities during erythropoiesis. Effect of erythropietin, vinblastine, colcemid, and daunomycin."; Experimental Cell Research; Mar. 15, 1975; vol. 91, No. 2, pp. 269-278.

* cited by examiner

*Primary Examiner*—Jeffrey Edwin Russel
(74) *Attorney, Agent, or Firm*—DLA Piper US LLP

(57) ABSTRACT

A drug conjugate comprising a targeting agent and an anti-cancer agent, wherein said targeting agent comprises an erythropoietin receptor ligand, is described. The drug conjugate can be used in methods of treating cancer. Also described are methods of treating cancer using the conjugate, methods of diagnosis, methods of imaging and pharmaceutical compositions.

14 Claims, 4 Drawing Sheets

Figure 1A:
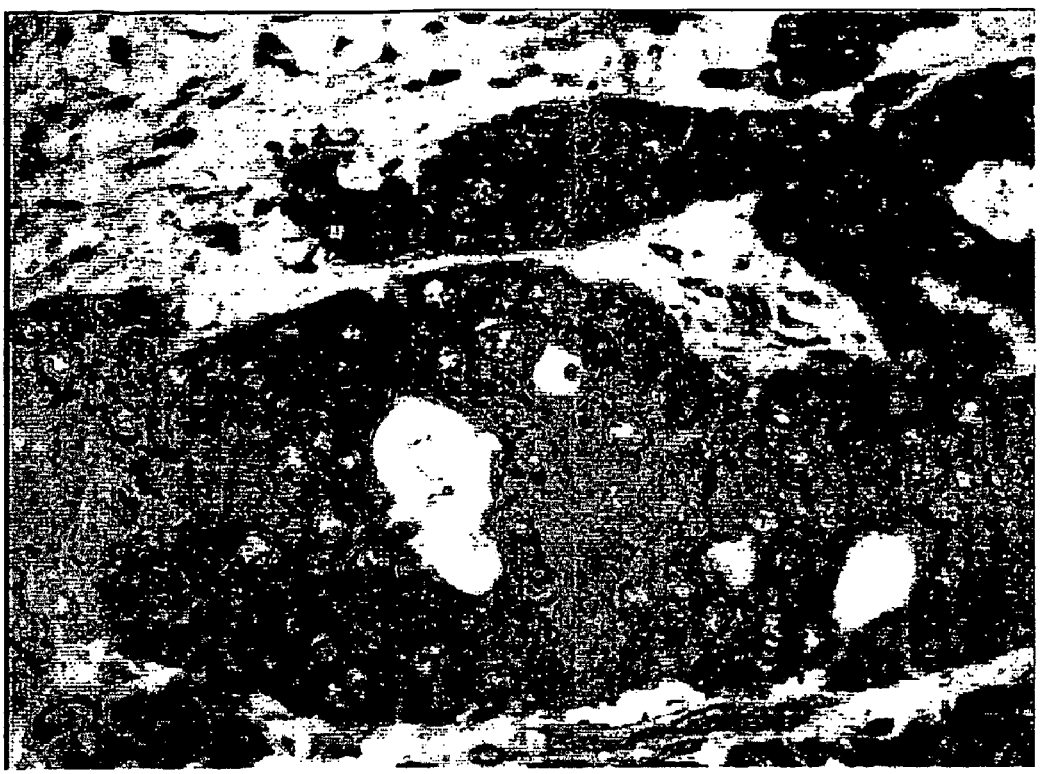

DRUG CONJUGATE COMPRISING AN ERYTHROPOIETIN RECEPTOR LIGAND AND AN ANTICANCER AGENT

FIELD OF THE INVENTION

This application relates to a medicament and its use in methods of treatment, diagnosis and imaging. In particular, it relates to the treatment of cancer with a cytotoxic agent linked to a targeting agent.

BACKGROUND TO THE INVENTION

This invention relates to anti-cancer medicaments that are specifically targeted to cancer cells by being linked to Erythropoietin (EPO) receptor ligands.

It is widely known in the field of oncology that the main disadvantage of chemotherapy is its inherent lack of specificity. Although anti-cancer drugs like Taxol™ are very successful in arresting cellular division in tumour cells, they also have the same effect on normal cells, giving rise to significant tissue and organ lesions, some of which are irreversible. Hence, it is essential to overcome this unspecific nature of chemotherapy so that the patient can tolerate it more and increase the efficiency of the drugs used.

EPO is a 30.4 kD Glycoprotein Hormone that is the main growth factor responsible for the regulation of red blood cell production in mammals (Erythropoiesis).

The primary site for the production of EPO in adult organisms is the kidney, although lower levels of EPO are synthesised by the liver and brain.

Synthesis of EPO itself in the body is regulated by oxygen tension in the body tissues, and is controlled by both positive and negative feedback signals. Low oxygen tension induces EPO production which in turn causes an increase in red blood cell production in the bone marrow. The enhanced oxygen supply to body tissues reduces EPO synthesis.

Recombinant human EPO is now readily available and is regularly used in the treatment of anaemia resulting from renal failure, harsh drug treatment like chemotherapy, and HIV-infection. The protein sequence for EPO, 193 amino acids in length, can be found in GenBank under Accession No. 1104303A (Jacobs et al. (1995) Nature 313,806-810), which is incorporated herein by reference in its entirety.

The protein sequence for the erythropoietin receptor, 508 amino acids in length, can be found in GenBank, under Accession No. AAA52403 (Jones et al. (1990) Blood 76,3135), which is also incorporated herein by reference in its entirety.

EPO circulates in the plasma at low concentrations (in pico-molar range) and binds to EPO-receptors (EPO-R) situated on the cell surface membrane. For many cells the receptor number is low, ranging from several hundred to several thousand of EPO-R per cell. Other cells can have high numbers of EPO-R in the order of 30,000 or greater.

The EPO Receptor is a 55 kD, (508 amino acid residue) transmembrane protein comprised of a 24 amino acid signal peptide, a 226 amino acid external segment, a 22 amino acid transmembrane segment, and a 236 amino acid cytoplasmic domain. This receptor is activated via a single EPO molecule bridging EPO receptor pairs. Binding of EPO to these EPO receptors causes a cascade of events including phosphorylation of the protein tyrosine kinase, Jak2. This in itself induces phosphorylation of the EPO receptors at 8 tyrosine residues. A vast array of other protein kinase signalling events are subsequently involved which ultimately cause the cell to express proteins involved in Erythropoiesis.

Recently Acs et al, Cancer Research 61, 3561-3565, 2001, reported that human breast cancer cells express the Erythropoietin (EPO) receptor. This result is confirmed herewith, but we surprisingly disclose additionally that other human tumours express the EPO receptor, which has led to the present invention.

SUMMARY OF THE INVENTION

As described herein, the present inventors have surprisingly shown that erythropoietin receptor expression is upregulated in cancer cells other than breast cancer cells. In particular, the inventors have shown that erythropoietin receptors are expressed in cells of lung cancer and non small cell lung cancers.

The demonstration that erythropoietin receptors are expressed on tumour cells at a supranormal level enables new methods of detecting and/or killing cancer cells in vitro or in vivo. In particular, it enables the targetting of cancer cells in a tissue.

According to a first aspect of the present invention, there is provided a drug conjugate comprising a targeting agent and an anti-cancer agent, wherein said targeting agent comprises an erythropoietin receptor ligand.

According to a second aspect of the invention, there is provided a method of killing cancer cells comprising contacting said cancer cells with a drug conjugate according to the first aspect of the invention.

The method of the second aspect of the invention can be used to kill cancer cells in vitro or in vivo. Thus, a third aspect of the invention provides a method of treating cancer, said method comprising administration of a therapeutically effective amount of a drug conjugate according to the first aspect of the invention to a mammal in need thereof.

In a fourth aspect, there is provided the use of a drug conjugate according to the first aspect of the invention in the preparation of a medicament for treating cancer.

According to a fifth aspect, there is provided a pharmaceutical composition for the treatment of cancer, wherein the composition comprises a drug conjugate according to the first aspect of the invention and a pharmaceutically acceptable excipient, diluent or carrier.

The presence of erythropoietin receptors on a tissue may be useful for the diagnosis of cancer or monitoring of progression of cancer. This may involve determining the number of EPO-receptors (and/or one or more isoforms and/or mutants of the erythropoietin receptor) on each cell or a population of cells.

Thus, according to a sixth aspect of the present invention, there is provided a method of diagnosis of the presence of cancer cells in a biological sample, said method including the step of contacting a ligand which binds to erythropoietin receptors with said sample and detecting binding of said ligand to cells of the sample.

In those tissues where erythropoietin receptors are not present on normal, non-cancerous cells, the detection of binding to erythropoietin receptors is indicative of the presence of cancer cells. In those tissue in which erythropoietin receptors are normally present, an increase in the level of expression is indicative of cancer.

The method of the sixth aspect of the invention may be performed in vitro or in vivo. In in vivo methods, the invention may be used to image tumours e.g. to detect the presence of or monitor the progression of cancer.

Thus, in a seventh aspect of the invention there is provided a method of imaging a cancer in a patient, said method comprising administering to the patient an erythropoietin receptor ligand coupled to an imaging agent, allowing said erythropoietin receptor ligand to bind to erythropoietin receptors and detecting the imaging agent.

The imaging agent may be any suitable agent. For example, the agent may be a paramagnetic ion or a radio-isotope. For example, where the patient is imaged using positron emission tomography, the imaging agent may be a positron emitter such as fluorine 18.

In this aspect of the invention, the ligand is labelled with any suitable imaging agent. Suitable imaging agents, e.g. for use with X-ray, PET etc are known in the art.

Indeed, in a further aspect of the present invention, there is provided an erythropoietin receptor ligand labelled by an imaging agent.

According to a further aspect of the current invention there is provided a medicament capable of avoiding efflux of the drug from the cancer cell by the Multi Drug Resistance (MDR) membrane glyco-protein, said medicament comprising a drug conjugate according to the first aspect of the invention. The problem of acquired resistance by tumour cells to drugs used in chemotherapy is a major problem today.

The drug conjugate, composition, medicament, uses and methods of the invention may be used for the treatment or diagnosis of any cancer. For example, the invention may be used in cancers of breast, cervix, uterus, ovary, prostate, brain, stomach or lung. In particularly preferred embodiments of the first aspect of the invention, the sample is from lung tissue. In a most preferred aspect of the present invention, the cancer is lung cancer and/or non-small cell lung carcinoma.

DETAILED DESCRIPTION

Drug Conjugates

As described above, the present invention provides a drug conjugate comprising a targeting agent and an anti-cancer agent, wherein said targeting agent comprises an erythropoietin receptor ligand. Any suitable drug conjugate may be used in the present invention. Drug conjugates and their effects may be tested using conventional methods. Known methods of identifying, verifying and testing ideal anticancer agent-ligand complexes for the EPO-receptors include Elisa and Surface Plasmon Resonance, e.g. Bia-Core™, dimerisation of EPO receptors can be used to give an indication of the functionality of the drug-ligand complex.

For example, Daunorubicin, may be chemically linked to an EPO receptor ligand, the EPO mimetic peptide EMP-1 for example.

Medicaments/conjugates may be screened using known methods, e.g. Elisa and Surface Plasmon Resonance, by analysing their binding to EPO receptors and inducing dimerisation of EPO receptor pairs. Preferably the drug-ligand complex is non-immunogenic.

Binding of the drug-ligand can cause sequestration of the EPO-receptor with its bound ligand and the linked drug into the cell cytoplasm, whereafter the ligand and its linked drug may be released from the receptor.

DETAILED DESCRIPTION

Ligands

In the context of the present invention, a "ligand" is a molecule which has binding specificity for another molecule, in particular the erythropoietin receptor. The ligand may be a member of a pair of specific binding members. The members of a binding pair may be naturally derived or wholly or partially synthetically produced. One member of the pair of molecules may have an area on its surface, which may be a protrusion or a cavity, which specifically binds to and is therefore complementary to a particular spatial and polar organisation of the other member of the pair of molecules. Thus, the members of the pair have the property of binding specifically to each other. Examples of types of binding pairs are antigen-antibody, biotin-avidin, hormone-hormone receptor, receptor-ligand, enzyme-substrate.

The present invention is concerned with receptor-ligand type reactions, although a binding member of the invention and for use in the invention may be any moiety, for example an antibody, which can bind to an erythropoietin receptor.

In preferred embodiments of the invention, the ligand is erythropoietin (EPO), an EPO analogue or fragment thereof or a functional mimetic of EPO.

An analogue of EPO or a fragment thereof means any polypeptide or antibody modified by varying the amino acid sequence of the EPO protein, e.g. by manipulation of the nucleic acid encoding the protein or by altering the protein itself. Such derivatives of the natural amino acid sequence may involve insertion, addition, deletion and/or substitution of one or more amino acids, preferably while providing a peptide having EPO activity, for example, erythropoietin receptor binding activity. Preferably such analogues involve the insertion, addition, deletion and/or substitution of 25 or fewer amino acids, more preferably of 15 or fewer, even more preferably of 10 or fewer, more preferably still of 4 or fewer and most preferably of 1 or 2 amino acids only.

Functional mimetics of EPO are substances which are not necessarily peptides and need not necessarily comprise the active portion of the amino acid sequence of EPO but which nevertheless retain biological activity of EPO.

A typical mimetic which may be used in the present invention is EMP-1, as described by Connolly et al, Bioorganic & Medicinal Chemistry Letters 10, 2000, 1995-1999.

Antibodies

The ligand may be an antibody. An "antibody" is an immunoglobulin, whether natural or partly or wholly synthetically produced. The term also covers any polypeptide, protein or peptide having a binding domain which is, or is homologous to, an antibody binding domain. These can be derived from natural sources, or they may be partly or wholly synthetically produced. Examples of antibodies are the immunoglobulin isotypes and their isotypic subclasses and fragments which comprise an antigen binding domain such as Fab, scFv, Fv, dAb, Fd; and diabodies.

The ligand of and for use in the invention may be an antibody such as a monoclonal or polyclonal antibody, or a fragment thereof. The constant region of the antibody may be of any class including, but not limited to, human classes IgG, IgA, IgM, IgD and IgE. The antibody may belong to any sub class e.g. IgG1, IgG2, IgG3 and IgG4.

As antibodies can be modified in a number of ways, the term "antibody" should be construed as covering any binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

Fragments of a whole antibody can perform the function of binding antigens. Examples of such binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341:544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., Science 242:423-426 (1988); Huston et al., PNAS USA 85:5879-5883 (1988)); (viii) bispecific single chain Fv dimers (PCT/US92/09965) and (ix) "diabodies", multivalent or multispecific fragments constructed by gene fusion (WO94/13804; P. Hollinger et al., Proc. Natl. Acad. Sci. USA 90:6444-6448 (1993)).

A fragment of an antibody or of a polypeptide for use in the present invention generally means a stretch of amino acid residues of at least 5 to 7 contiguous amino acids, often at least about 7 to 9 contiguous amino acids, typically at least about 9 to 13 contiguous amino acids, more preferably at least about 20 to 30 or more contiguous amino acids and most preferably at least about 30 to 40 or more consecutive amino acids.

The term "antibody" includes antibodies which have been "humanised". Methods for making humanised antibodies are known in the art. Methods are described, for example, in Winter, U.S. Pat. No. 5,225,539. A humanised antibody may be a modified antibody having the hypervariable region of a monoclonal antibody and the constant region of a human antibody. Thus the binding member may comprise a human constant region.

The variable region other than the hypervariable region may also be derived from the variable region of a human antibody and/or may also be derived from a monoclonal antibody. In such case, the entire variable region may be derived from murine monoclonal antibody and the antibody is said to be chimerised. Methods for making chimerised antibodies are known in the art. Such methods include, for example, those described in U.S. patents by Boss (Celltech) and by Cabilly (Genentech). See U.S. Pat. Nos. 4,816,397 and 4,816,567, respectively.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementary determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

Anti-Cancer Agents

Any suitable chemotherapeutic agent or agents may be used as the anti-cancer agent in the present invention.

The agent may be any kind of drug or peptide or piece of DNA or RNA that inhibits cellular division, or causes apoptosis.

For example, the agent for use in the invention may include but is not limited to: Anthracycline Antibiotic, Daunorubicin, Doxorubicin, Taxol™, 5-Fluorouracil (5 FU), Leucovorin, Irinotecan, Idarubicin, Mitomycin C, Oxaliplatin, Raltitrexed, Tamoxifen and Cisplatin, Actinomycin D, Mitoxantrone or Blenoxane or Mithramycin.

In one preferred embodiment, the agent is a DNA chelator. More preferably the agent is an Anthracycline Antibiotic. Even more preferably the drug is Doxorubicin or Idarubicin. Most preferably the drug is Daunorubicin.

In another preferred embodiment, the agent is Actinomycin D Mitoxantrone or Blenoxane or Mithramycin.

In another preferred embodiment the agent is a cytoskeletal binding drug. Even more preferably the drug is paclitaxel (Taxol™).

The agent can also be a member of the Bio-Reductive drugs that are activated under hypoxic cellular conditions. Suitable BioReductive drugs include SR4233 or AQ4N.

The ligand may be linked to one or more anti-cancer agent molecules, which may be the same or different.

Preferably the ligand has more than one agent molecule linked to it.

Linkers

The anti-cancer agent may be linked to the ligand by any suitable means. For example, the anti-cancer agent-ligand link may be an amine bond. In one embodiment, the drug-ligand link comprises two or more amino acids.

More preferably the drug-ligand link is via bi-functional chemical cross linkers, like Pierce™ DSP, DVP and the like.

Preferably, the drug-ligand amino acid link is cleavable, for example an ester band, cleavable by intracellular esterases.

Preferably the link is cleavable under low oxygen tensions, i.e. sensitive to the cytoplasmic REDOX state, in order to increase the toxicity of the drug in the cell.

For the purpose of this invention, "linker" is defined as a chemical compound which can form a covalent bond with an anti-cancer agent and another covalent bond with the ligand on the other hand. Preferably, a linker used in practising the present invention should have a suitable length and should not have a significant effect on the anticancer agent's therapeutic property or the erythropoietin receptor ligand's specific affinity to the erythropoietin receptors on the targeted tumor cells.

Of course, the choice of a linker in a specific practice depends on what type of anti-cancer drug it is to be conjugated to. For example, if the anti-cancer drug has a —OH group or a —NH$_2$ group for connecting a linker, the linker should preferably have a —COOH group so that an ester bond can be formed between the —OH and —COOH groups or a peptide bond can be formed between the —NH$_2$ and —COOH; if the anti-cancer drug has a —COOH group for connecting a linker, then the linker should preferably have a free —NH$_2$ group (in addition to the —NH$_2$ group which forms a peptide bond with the erythropoietin receptor ligand) so that a peptide bond can be formed between the —COOH and —NH$_2$ groups.

If the anti-cancer drug has a maleimide group, the linker should preferably have a free —SH group so that a covalent S-maleimide bond can be formed (and, vice versa, if the anti-cancer agent has an —SH group, the linker should have a maleimide group).

The conjugation between a maleimide group and a sulfhydryl group (—SH) has an additional advantage because the overall synthesis yield is increased as the conjugation can be conducted after the peptide cleavage and deprotection. This can prevent the anti-cancer drug from TFA treatment in the peptide cleavage and deprotection step.

In a preferred embodiment of the invention, maleimide is used as a linker group. In one preferred embodiment, the maleimide group is attached to the 3' amino position of the anti-cancer agent daunorubicin, e.g. via a benzamide bond. In another preferred embodiment, the maleimide group is attached to the 13 keto group of the anti-cancer agent daunorubicin.

In further embodiments, the formation of stable, covalently linked conjugates with fully retained biological activities of an anticancer drug may be achieved by using a di-carboxylic acid linker, such as glutaric acid. One carboxyl group of the linker group forms an ester bond with the anticancer agent e.g the 2'-OH group of paclitaxel or the —OH groups of other anticancer drugs and the other carboxyl group of the linker group forms a carboxamide bond with a well chosen free amino group of the peptide carrier, such as an erythropoietin analogue.

Because some anti-cancer drugs, such as paclitaxel, have poor water solubility, a conjugated drug-linker-erythropoietin receptor ligand complex can have a free —$NH_2$ group for further connection to a component which can improve the drug's water solubility. For instance, the —$NH_2$ can be connected to a PEG, sugar or biotin group Moreover the erythropoietin receptor may be linked to the anticancer agent indirectly e.g. via liposomes, where the erythropoietin receptor ligand is covalently connected to a compound which then forms liposomes, where one or more anti-cancer agents can be disposed. The anticancer agent in the liposomes will be released once the conjugated erythropoietin receptor ligand brings the liposomes to the targeted tumor cells.

Treatment

"Treatment" includes any regime that can benefit a human or non-human animal. The treatment may be in respect of an existing condition or may be prophylactic (preventative treatment). Treatment may include curative, alleviation or prophylactic effects.

"Treatment of cancer" includes treatment of conditions caused by cancerous growth and includes the treatment of neoplastic growths or tumours. Examples of tumours that can be treated using the invention are, for instance, sarcomas, including osteogenic and soft tissue sarcomas, carcinomas, e.g., brain, breast-, lung-, bladder-, thyroid-, prostate-, colon-, rectum-, pancreas-, stomach-, liver-, uterine-, cervical and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas.

In preferred embodiments, the present invention is used and is useful for the treatment of one or more of breast cancer, cancer of the kidney, brain cancers, lung cancer and non small cell lung carcinoma. In particularly preferred embodiments, the present invention is used and is useful for the treatment of lung cancer and/or non small cell lung carcinoma.

The conjugates, compositions and methods of the invention may be particularly useful in the treatment of existing cancer and in the prevention of the recurrence of cancer after initial treatment or surgery.

Administration

Conjugates and compositions of and for use in the present invention may be administered to a patient in need of treatment via any suitable route. The precise dose will depend upon a number of factors, including the precise nature of the conjugate and and/or anticancer agent and/or the nature and site of the cancer.

Some suitable routes of administration include (but are not limited to) oral, rectal, nasal, topical (including buccal and sublingual), vaginal or parenteral (including subcutaneous, intramuscular, intravenous, intradermal, intrathecal and epidural) administration. Intravenous administration is preferred.

It is envisaged that injections (intravenous) will be the primary route for therapeutic administration of conjugates and compositions although delivery through a catheter or other surgical tubing is also envisaged. Liquid formulations may be utilised after reconstitution from powder formulations.

In one embodiment, where, for example, the conjugates or compositions are used for the treatment of bladder cancer, it is envisioned that the conjugate or composition is administered using a bladder wash technique.

In a further preferred embodiment, in particular for the treatment of cancers of the lung, the conjugate is formulated for delivery via aerosol, so that the drug-ligand complex can access the EPO receptors facing into the lumen of the bronchus or lungs. This prevents the need for introducing excessive amounts of EPO or ligand into the blood stream, which would down-regulate EPO receptor synthesis by erythropoietic cells.

Where the cancer is of the GI tract, the drug-ligand conjugate is preferably ingested to access the EPO receptors facing the lumen of the digestive tract.

For intravenous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

In a preferred embodiment, they are administered as a pharmaceutical composition, which will generally comprise a suitable pharmaceutical excipient, diluent or carrier selected dependent on the intended route of administration.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The conjugate or composition may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982). Liposomes are prepared by well-known methods: DE 3,218, 121A; Epstein et al, PNAS USA, 82: 3688-3692, 1985; Hwang et al, PNAS USA, 77: 4030-4034, 1980; EP-A-

0052522; E-A-0036676; EP-A-0088046; EP-A-0143949; EP-A-0142541; JP-A-83-11808; U.S. Pat. Nos. 4,485,045 and 4,544,545. Ordinarily, the liposomes are of the small (about 200-800 Angstroms) unilamellar type in which the lipid content is greater than about 30 mol. % cholesterol, the selected proportion being adjusted for the optimal rate of the constituent leakage.

Examples of the techniques and protocols mentioned above and other techniques and protocols which may be used in accordance with the invention can be found in Remington's Pharmaceutical Sciences, 16th edition, Oslo, A. (ed), 1980.

The conjugate or composition may be administered in a localised manner to a tumour site or other desired site.

Pharmaceutical Compositions

As described above, the present invention extends to a pharmaceutical composition for the treatment of cancer, the composition comprising composition comprises a drug conjugate according to the first aspect of the invention and a pharmaceutically acceptable excipient, diluent or carrier. Pharmaceutical compositions according to the present invention, and for use in accordance with the present invention may comprise, in addition to active ingredients, a pharmaceutically acceptable excipient, carrier, buffer stabiliser or other materials well known to those skilled in the art.

Such materials should be non-toxic and should not interfere with the efficacy of the active ingredient. The precise nature of the carrier or other material will depend on the route of administration, which may be oral, or by injection, e.g. intravenous.

The formulation may be a liquid, for example, a physiologic salt solution containing non-phosphate buffer at pH 6.8-7.6, or a lyophilised powder.

Dose

The conjugates or compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration.

It is anticipated that in embodiments of the invention the conjugate or composition could be given in combination with other forms of chemotherapy or indeed radiotherapy. The conjugates and/or compositions of the invention may be administered simultaneously, separately or sequentially with the other form of chemotherapy or radiotherapy.

Figure 1B:
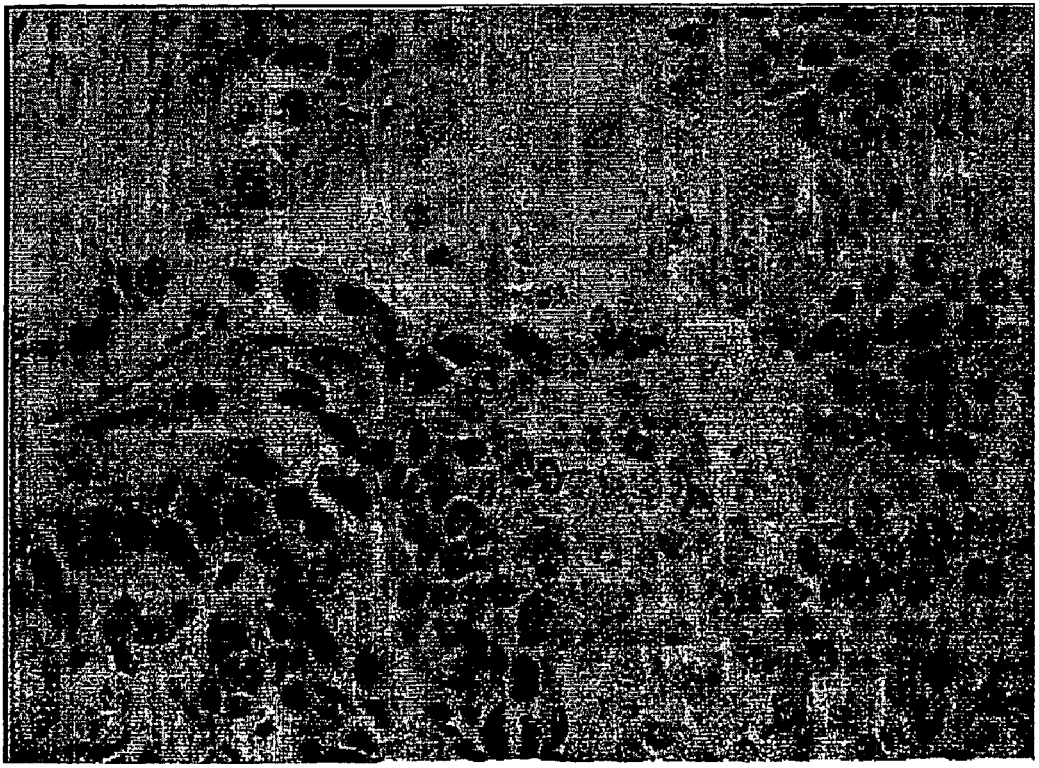

The invention will now be described further in the following non-limiting examples. Reference is made to the accompanying drawings in which:

FIG. 1a is a micrograph of a Breast Cancer sample section staining positive (HRPO) for the EPO Receptor at the periphery of the cell FIG. 1b is a negative control, using the secondary antibody only (Rabbit anti-mouse) antibody.

Figure 2A:
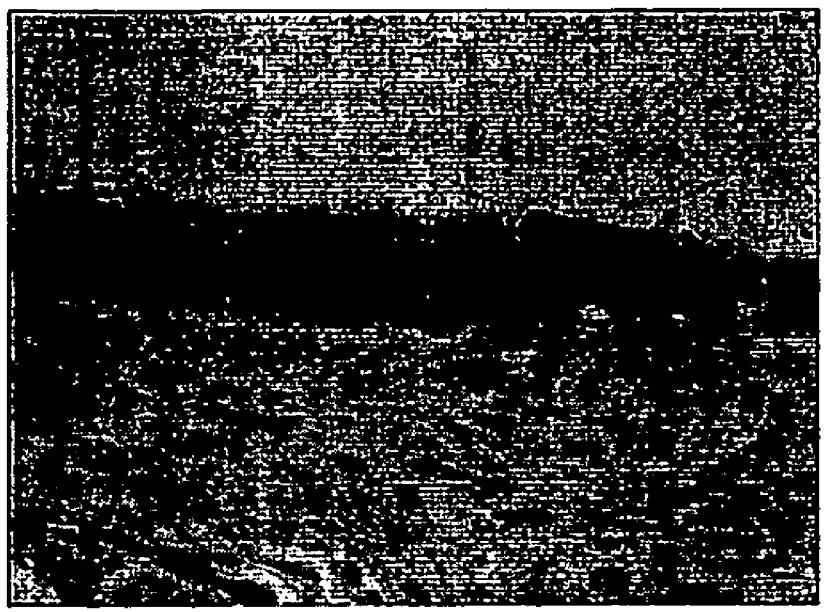
Figure 2B:
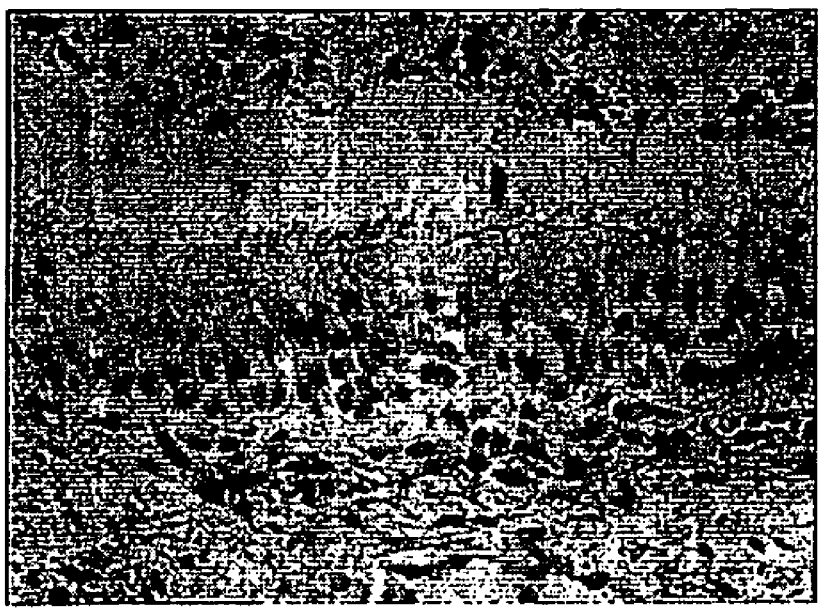
Figure 3A:
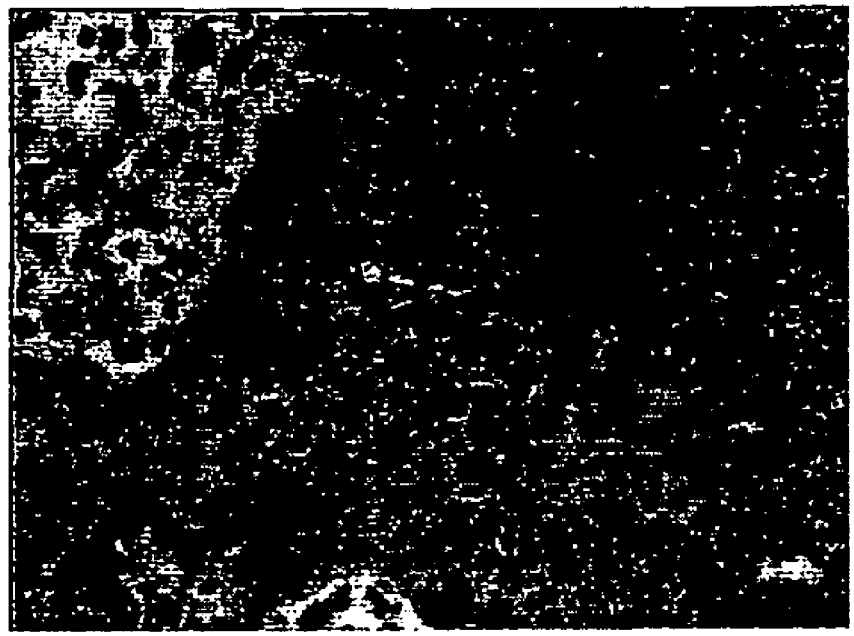
Figure 3B:
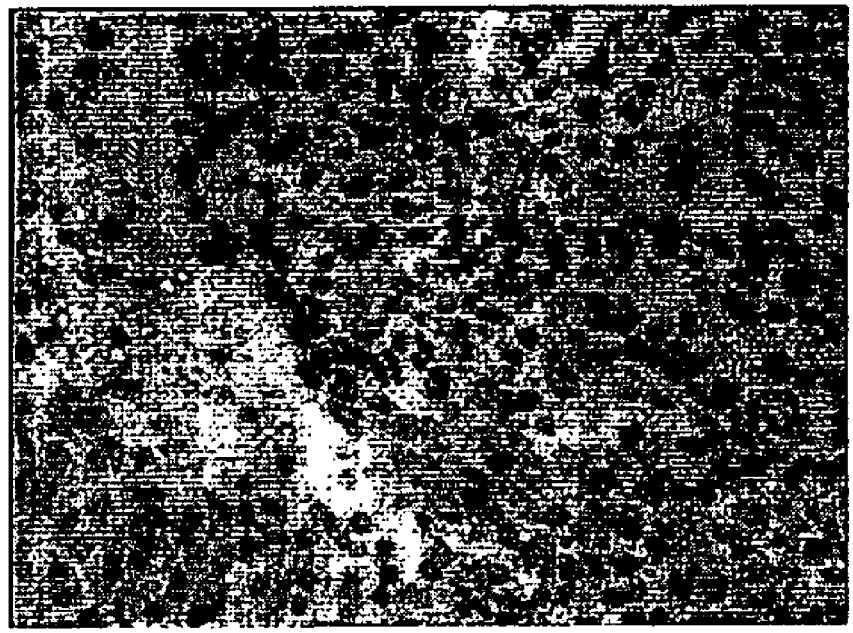
Figure 4:
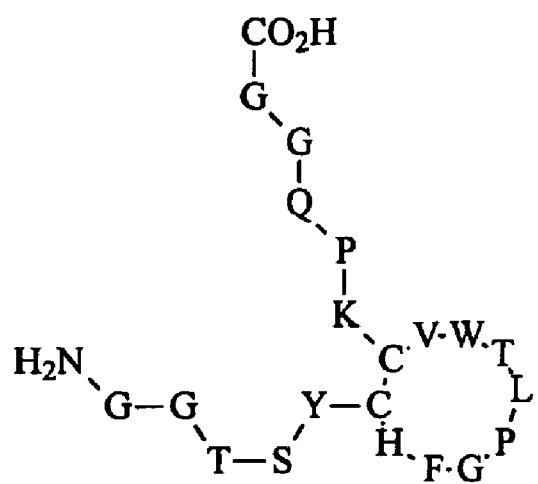

FIG. 2a is a micrograph of a section from a human lung cancer biopsy, staining positive for the EPO receptor in the epithelial cilia; and FIG. 2b is a micrograph of a serial section negative control from the same biopsy sample as in FIG. 2a; and FIG. 3a is a micrograph of a Non Small Cell Lung Cancer also showing specific staining for the EPO receptor; and FIG. 3b is a serial section negative control of the sample of FIG. 3a; and FIG. 4 is a diagrammatic representation of the EPO-mimetic EMP-1 represented by SEQ ID NO: 1.

Figure 5:
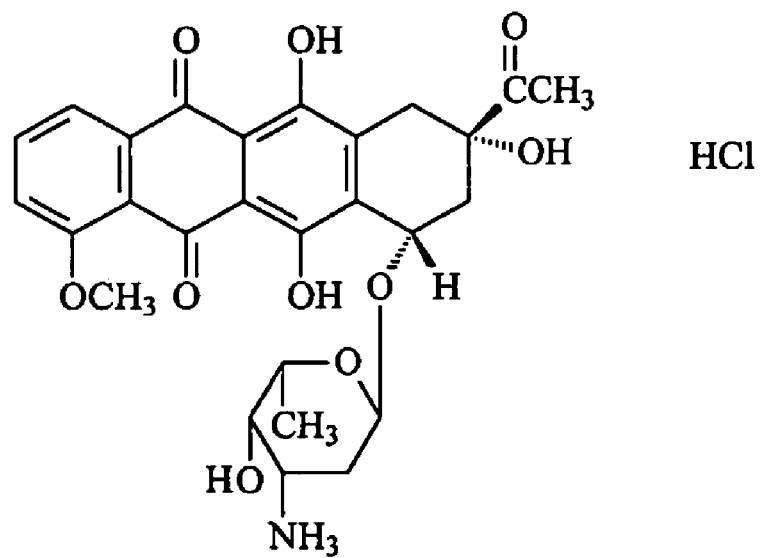

FIG. 5 is a diagramatic representation of the anti-cancer drug daunorubicin.

EXAMPLE 1

Human tumour Cells Demonstrate Enhanced Expression of EPO Receptors

The following data demonstrate that human tumour cells express EPO receptors and that this can be used as a novel way of selectively targeting drugs to cancer cells.

With reference to FIG. 1a and FIG. 1b, the tumour cells of FIG. 1a are immunohistochemically positive for the EPO receptor and where there is normal surrounding tissue, the cells are completely free of stain. FIG. 1b is a negative control (i.e. without the primary rabbit anti-human EPO receptor antibody).

FIGS. 2a, 2b, 3a and 3b now demonstrate that EPO receptor expression is not limited to breast cancer cells but is also found in Bronchial Epithelium of a lung cancer, see FIG. 2a, where EPO receptor expression is found polarised to the upper compartment of the epithelium, i.e. cilia. Some nuclear crowding is apparent, but otherwise the morphological pattern is normal. FIG. 2b is clearly negative for the EPO receptor.

Additionally, FIG. 3a shows EPO receptor expression in a section form a patient with Non Small Cell Lung Carcinoma. Loss of cell polarity is evident in the malignant epithelial cells. Some of the tumour cells are cytoplasmically positive for the EPO receptor (EPO-R). Areas of necrosis also show definite EPO-R positivity which may indicate macrophage involvement. FIG. 3b is also clearly negative for the EPO receptor.

The lack of expression of EPO receptors by the surrounding normal tissue clearly demonstrates that drugs may be specifically targetted to cancer cells by linking them to erythropoietin receptor ligands such as EPO or EPO fragments or mimetic peptides.

EXAMPLE 2

Production of Conjugates a) 3'Amino Maleimide Daunorubicin Derivative-EPO Conjugate A daunorubicin-EPO conjugate is prepared as follows. A maleimide derivative of daunorubicin is prepared by reacting daunorubicin.HCl with 3-maleimidobenzoic acid chloride and two equivalents of triethylamine in THF for 15 h at room temperature in the dark. Isolation of the compound is performed by chromatography on silica gel (THF/hexane 3/1) and subsequent chromatography on a LiChroPrepDiol column(Merck) (THF/hexane 3/1) to obtain a pure sample of the daunorubicin maleimide derivative in which the maleimide group is at the 3'amino position of daunorubicin.

The daunorubicin derivative is then reacted with a mutant erythropoietin comprising an additional cysteine group for binding to the double bond of the maleimide group of the daunorubicin derivative to form the drug conjugate.

The drug-ligand complex is then tested for activity using cultured non small cell lung carcinoma cells. The ability of the cells to endocytose the conjugates are determined.

Binding of the conjugates to the EPO receptor on the surface of the cancer cell, followed by sequestration of the conjugate into the cell cytoplasm, and its release from the EPO receptor therein, enables the Daunorubicin drug to retain its activity and interchelate the DNA, forms DNA breaks and catalyse the formation of free radicals.

Other methods of verifying activity of the conjugate for the EPO-receptors include Elisa and Surface Plasmon Resonance, e.g. Bia-Core™, dimerisation of EPO receptors will give an indication of the functionality of the drug-ligand complex.

Incorporation of the medicaments into the cancer cells is carried out using standard in vitro cell culture and radiolabelling techniques. Resistance to efflux via the MDR protein in cancer cell lines that express this protein is also analysed using the above mentioned methods.

b) 13 Keto Maleimide Daunorubicin Derivative-EPO Conjugate

A 13-keto maleimide daunorubicin derivative-EPO conjugate is prepared as follows. A maleimide derivative of daunorubicin is prepared by reacting daunorubicin.HCl with a five-fold excess of 3-maleimidobenzoic acid hydrazide (trifluoroacetate salt) in anhydrous methanol, addition of catalytic amounts of $CF_3COOH$ and stirring for 96 h at room temperature in the dark. The products are precipitated by repeated addition of acetonitrile. Analytical samples are obtained by crystallisation from methanol/acetonitrile to obtain a pure sample of the daunorubicin maleimide derivative in which the maleimide group is at the 13 keto position of daunorubicin.

The conjugate produced is tested as described for the 3'amino derivative conjugate as described in part (a).

All documents referred to in this specification are herein incorporated by reference. Various modifications and variations to the described embodiments of the inventions will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the art are intended to be covered by the present invention.

The invention claimed is:

1. A drug conjugate comprising a targeting agent and an anti-cancer agent, wherein said targeting agent comprises an erythropoietin receptor ligand and said anti-cancer agent is selected from the group consisting of:

drugs that inhibit cellular division, drugs that cause apoptosis,

DNA chelators, cytoskeletal binding drugs, and bio-reductive drugs that are activated under hypoxic cellular conditions.

2. The drug conjugate according to claim 1, wherein said anti-cancer agent is Daunorubicin or a derivative thereof, Anthracycline Antibiotic, Doxorubicin, Idarubicin, Paclitaxel, 5-Flurouracil, Leucovorin, Irinotecan, Mitomycin C, Oxaliplatin, Raltitrexed, Tamoxifen, Cisplatin, Actinomycin D, Mitoxantrone, Blenoxane, Mithramycin, SR4233, or AQ4N.

3. The drug conjugate according to claim 1, wherein-said anti-cancer agent is a maleimide derivative of daunorubicin.

4. The drug conjugate according to claim 1, wherein said erythropoietin receptor ligand is erythropoietin (EPO), an EPO analogue or fragment thereof or a functional mimetic of EPO.

5. A method of killing cancer cells that express an erythropoietin receptor, comprising contacting said cancer cells with a drug conjugate according to claim 1.

6. A method of treating cancer that expresses an erythropoietin receptor, comprising administration of a therapeutically effective amount of a drug conjugate according to of claim 1 to a mammal in need thereof.

7. A pharmaceutical composition for the treatment of cancer that expresses an erythropoietin receptor, wherein the composition comprises a drug conjugate according to claim 1 and a pharmaceutically acceptable excipient, diluent or carrier.

8. A method of imaging a cancer that expresses an erythropoietin receptor in a patient, comprising; administering to the patient an erythropoietin receptor ligand coupled to an imaging agent; allowing said erythropoietin receptor ligand to bind to erythropoietin receptors; and detecting the imaging agent.

9. The method of claim 8, wherein said imaging agent is a paramagnetic ion or a radioisotope.

10. The method of claim 8, wherein said cancer is imaged by positron emission tomography (PET).

11. A medicament capable of avoiding efflux of a drug from a cancer cell that expresses an erythropoietin receptor by Multi Drug Resistance (MDR) membrane glyco-protein, comprising the drug conjugate according to claim 1.

12. The conjugate according to claim 1 wherein said cancer is lung cancer or non-small cell lung carcinoma.

13. The pharmaceutical composition according to claim 7, wherein said cancer is lung cancer or non-small cell lung carcinoma.

14. The medicament according to claim 11, wherein said cancer is lung cancer or non-small cell lung carcinoma.

* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial sequence
<220> FEATURE:
<223> OTHER INFORMATION: EPO mimetic peptide 1 (EMP1), a synthetic
      peptide agonist of the EPO receptor

<400> SEQUENCE: 1

Gly Gly Thr Ser Tyr Cys His Phe Gly Pro Leu Thr Trp Val Cys Lys
1               5                   10                  15

Pro Gln Gly Gly
            20
```